United States Patent [19]

Beard et al.

[11] Patent Number: 4,854,865
[45] Date of Patent: Aug. 8, 1989

[54] BIOCOMPATIBLE ELECTRODE AND USE IN ORTHODONTIC ELECTROOSTEOGENESIS

[75] Inventors: Richard B. Beard, Atco, N.J.; Saleem Hasan, Philadelphia, Pa.; Kevin J. Scoles, Ardmore, Pa.; Banu Onaral, Philadelphia, Pa.

[73] Assignee: Drexel University, Philadelphia, Pa.

[21] Appl. No.: 118,368

[22] Filed: Nov. 6, 1987

[51] Int. Cl.$^4$ .............................................. A61C 7/00
[52] U.S. Cl. ...................................................... 433/18
[58] Field of Search ............... 433/173, 174, 175, 176; 128/803, 798, 802, 639, 640, 641

[56] References Cited

U.S. PATENT DOCUMENTS

| | | |
|---|---|---|
| 2,151,905 | 3/1939 | Emmert . |
| 2,319,259 | 5/1943 | Peterson . |
| 3,118,450 | 1/1964 | Freeman et al. . |
| 3,254,279 | 5/1966 | Cohn et al. . |
| 3,981,724 | 9/1976 | Prasad . |
| 4,153,060 | 5/1979 | Korostoff et al. . |
| 4,270,543 | 6/1981 | Tabuchi et al. . |
| 4,299,231 | 11/1981 | Karmann et al. . |
| 4,380,528 | 4/1983 | Shevakin et al. . |
| 4,406,827 | 9/1983 | Carim . |
| 4,414,143 | 11/1983 | Felten . |
| 4,448,199 | 5/1984 | Schmid . |
| 4,465,074 | 8/1984 | Bochziter ........................ 128/803 |
| 4,519,779 | 5/1985 | Lieb .................................. 433/18 |
| 4,570,637 | 2/1986 | Gomes et al. . |
| 4,622,975 | 11/1986 | Danby et al. . |
| 4,676,257 | 6/1987 | Halpern ........................... 128/803 |
| 4,702,732 | 10/1987 | Powers et al. .................. 128/803 |

FOREIGN PATENT DOCUMENTS 57-186163  5/1981  Japan .
1032272  2/1963  United Kingdom .

OTHER PUBLICATIONS

Zeev Davidovitch, "Electric Currents, Bone Remodeling, and Orthodontic Tooth Movement: I. The Effect of Electric Currents on Periodontal Cyclic Nucleotides", Am. J. Orthod., 77(1):14–32 (1980).

Zeev Davidovitch, "Electric Currents, Bone Remodeling, and Orthodontic Tooth Movement: II. Increase in Rate of Tooth Movement a Periodontal Cyclic Nucleotide Levels by Combined Force and Electric Current", Am. J. Orthod., 77(1):33–45 (1980).

Primary Examiner—Robert Peshock
Attorney, Agent, or Firm—Panitch Schwarze Jacobs and Nadel

[57] ABSTRACT

An improved method of orthondontic electroosteogenesis comprises providing a biocompatible anode having a noble metal portion in engagement with an electrolytic gel portion comprising agarose and an electrolyte, where the anode gel portion is in engagement with epithelial gingiva at an area of osteoclastic or osteoblastic activity, and a biocompatible cathode having a noble metal portion in engagement with an electrolytic gel portion comprising agarose, an electrolyte, and a weak, biocompatible acid, where the cathode gel portion is in engagement with epithelial gingiva at an area of osteoblastic or osteoclastic activity. Electric current is then applied across the anode and cathode to stimulate osteogenesis. The invention also comprises biocompatible electrodes for electric stimulation of tissue.

36 Claims, 1 Drawing Sheet

BIOCOMPATIBLE ELECTRODE AND USE IN ORTHODONTIC ELECTROOSTEOGENESIS

FIELD OF THE INVENTION

The present invention relates generally to an improved method of orthodontic electroosteogenesis and, more particularly, to an improved method that employs a biocompatible anode and cathode. The invention also relates to biocompatible electrodes generally.

BACKGROUND OF THE INVENTION

Orthodontic appliances or "braces" are common devices employed by orthodontists to correct or enhance tooth movement and growth in the human patient. Orthodontic appliances are typically attached to the tooth or teeth to be moved and corrective forces are applied to the appliance by means of springs, elastics, and other devices known in the art.

The mechanism by which mechanical ortho appliances function is fairly straightforward. Force is applied in the direction towards which it is desired to have tooth movement. Initially, spaces around the teeth and the elastic nature of the epithelial gingiva surrounding each tooth allow for considerable movement on the order of about 0.5 to about 1 mm. At this point, the tooth becomes compressed against the mandibular or maxillary bone. As the force continues to be applied, compressed bone cells undergo osteoclasty, i.e., bone re-absorption, and bone cells filling in the gap created by and behind the tooth movement undergo osteoblasty, i.e., bone growth. These processes are typically observed as tooth movement, followed by a lag time, followed again by tooth movement and so on until the ortho force is halted when the desired repositioning has occurred.

While these traditional, mechanical ortho appliances and techniques are generally effective, there are several deficiencies and drawbacks in their use. For example, mechanical ortho appliances generally require a wearing time on the order of several years with forces being changed every few weeks. In addition, ortho appliances are often cumbersome and uncomfortable. Given the length of time certain appliances must be worn, such discomfort can be substantial and prolonged.

It is desirable in the art to reduce the lag time present in ortho movement and thereby decrease the time necessary for a patient to wear an ortho appliance. Korostoff and Davidovitch disclosed in United States Patent No. 4,153,060, "Method and Apparatus for Electrically Enhanced Bone Growth and Tooth Movement," the feasibility of using electrical orthodontics to decrease the overall time required to move a tooth orthodontically. Korostoff and Davidovitch demonstrated that, by using an electric stimulation with an ortho force, the overall time required to move a tooth orthodontically could be reduced significantly. In addition, such electric stimulation techniques could potentially be used for correcting other oral bone growth malformations, such as cleft pallet.

While the methods in the prior art have great promise, one major difficulty and deficiency has been poor biocompatibility of the stimulating electrodes. Biocompatibility at the interface between stimulating electrodes and the tissue with which the electrodes are in contact, is desirable for meaningful use of electro-stimulating ortho appliances. Poor biocompatibility of the electrodes in orthodontic appliances results in severe lacerations, ulcerations, irritation and swelling of the epithelial gingiva.

Attempts in the prior art to use noble metal electrodes, such as gold, silver, platinum, palladium, as well as stainless steel, proved to lack biocompatibility. Moreover, attempts in the prior art to utilize a gel interface between the electrode and the tissue using, for example, agar and agar solutions, yielded a similar lack of biocompatibility.

Noble metal electrodes used with an agar gel interface were found to deteriorate under use. For example, U.S. Pat. No. 4,570,637 of Gomes and Massione discloses that silver electrodes using an electrically conductive gel, such as an agar solution of sodium chloride, when subjected to DC current, are ionized and the silver is converted to silver chloride. This conversion causes an increased resistance and renders the electrode useless for biomedical purposes. In addition, experiments indicate that noble metals, such as silver, when ionized, migrate across such agar gel interfaces and react adversely with the gingiva.

The present invention overcomes many of the disadvantages inherent in the methods of electric stimulation of tissues described above by providing a biocompatible anode and a biocompatible cathode for use in orthodontic electroosteogenesis, particularly where relatively high electric currents are employed. The present invention significantly reduces gingival irritation, such as tissue laceration, and increases appliance wearability and patient comfort.

SUMMARY OF THE INVENTION

Briefly stated, the present invention includes an improved method of orthodontic electroosteogenesis by providing a biocompatible anode having a noble metal portion in engagement with an electrolytic gel portion comprising agarose and an electrolyte, whereby the gel portion of the anode is placed in engagement with epithelial gingiva at an area adjacent to a tooth to be repositioned, providing a biocompatible cathode having a noble metal portion in engagement with an electroytic gel portion comprising agarose, an electrolyte and a weak, biocompatible acid, whereby the gel portion of the cathode is placed in engagement with epithelial gingiva at an area adjacent to a tooth to be repositioned, and where electric current is applied across the cathode and anode to stimulate osteoclasty and osteoblasty.

In addition, the present invention further comprises a biocompatible electrode for electric stimulation which comprises material having a noble metal portion in engagement with an electrolytic gel portion, whereby the gel comprises agarose, an electrolyte and, in one embodiment, a weak, biocompatible acid.

BRIEF DESCRIPTION OF THE DRAWING

For the purpose of illustrating the invention, there is shown in the drawing a form which is presently preferred; it being understood, however, that this invention is not limited to the precise arrangements and instrumentalities shown.

DESCRIPTION OF PREFERRED EMBODIMENTS

Figure 1:
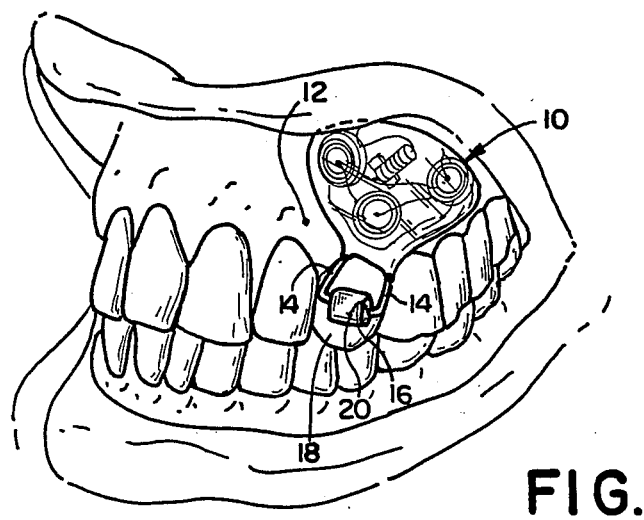
FIG. 1 is a perspective view of a section of the human mouth showing an application of the present invention.

Referring to the drawing, wherein like numerals indicate like elements throughout, there is shown in FIG. 1 a perspective view of a section of the human mouth showing an embodiment of the present invention, whereby a paddle 10 containing a cathode and an anode is placed in engagement with the epithelial gingiva 12 of the mouth, and where two prongs 14 extend from the paddle 10 to a bracket 16 fastened on an adjacent tooth 18. The gingiva 12 is largely non-keratinized epithelial tissue surrounding the teeth and kept generally moist by the saliva of the mouth. Such tissue is friable and sensitive, and its shape generally depends upon the formation of the underlying teeth and bone.

The paddle 10, shown in more detail in FIGS. 2, 3 and 4, consists primarily of material durable enough to maintain the integrity of its shape, and hold the prongs 14, electrodes and other electric components, described below, in place. One such material is methyl methacrylate, commonly known as dental acrylic. Methyl methacrylate is an acrylic resin polymer widely used in orthodontic appliances by those skilled in the art. Dental acrylic allows for simple shaping and maintains excellent structural integrity. It will be apparent to those skilled in the art, however, that analogous materials may be used in place of dental acrylic.

The shape of the paddle 10 is determined by the area of gingiva 12 at which the paddle 10 is to be placed. The gingiva surrounding the tooth or teeth 18 to be moved dictates the desired shape of the paddle 10. Proper shaping of the paddle 10 is desirable to avoid irritation to the patient. Typically, an orthodontist determines this shape by taking impressions of the gingiva 12 to be covered and using such impressions as a mold for the paddle 10 using methods and materials known in the art.

The dimensions of the paddle depend upon the size of the area of gingiva 12 to be covered, the size and shape of the patient's mouth, the size and shape of the electrodes and other electric components to be used, the size and number of prongs 14 to be used, as determined by the orthodontist, as well as other factors. Preferably, the paddle 10 should be large enough to position electrodes with a surface area at the electrode/gingiva interface of about 10 mm$^2$ per electrode as described below. However, it will be apparent to those skilled in the art that larger or smaller electrode surface areas may be employed.

It is preferred that the paddle 10 be positioned so that the anode, discussed below, contained in the paddle 10 is in engagement with an area of gingiva 12 covering a region of osteoclasty and the cathode, discussed below, contained in the paddle 10 is in engagement with an area of gingiva 12 covering a region of osteoblasty. It is particularly preferable that the electrodes are in engagement with non-keratinized gingiva 12.

The bracket 16 is of any suitable type commonly used by orthodontists, such as the "Rocky Mountain" bracket manufactured by the company of the same name. The bracket 16 may be fastened to the tooth 18 by adhesive, such as dental epoxy, or may be attached to a band (not shown), which, in turn, is attached to the tooth 18. The bracket 16 serves to hold the paddle 10 in place in engagement with the gingiva 12 and allows for easy insertion and removal of the paddle 10 by inserting the prongs 14 into the tube 20 on the bracket 16.

The prongs 14, which are anchored in the paddle 10 by means known in the art, may be comprised of ortho wire commonly used by those skilled in the art in conjunction with ortho appliances for application of ortho forces and as guides for tooth movement. Ortho wire of various cross sectional geometries is maleable by an orthodontist using materials and techniques known in the art, and maintains its configuration for periods as long as weeks or months with little maintenance. In one embodiment, the ortho wire is 0.025 inch circular stainless steel, although it will be apparent to those skilled in the art that other dimensions, geometric shapes and analogous materials may be employed.

The bracket 16 may also be attached to an ortho force, such as an elastic or spring device (not shown) used to reposition the tooth 18. Each paddle 10, bracket 16 and set of prongs 14 will be shaped and positioned for the individual tooth 18 and gingiva 12 of a given patient, as would any ortho appliance used and prescribed by one skilled in the art.

The electrodes are held in engagement with the gingiva 12 by the prongs 14, which are attached to the bracket 16 and anchored in the paddle 10 in which the anode 22 and cathode 24 are held, and by the cheek (not shown) and/or lip of the patient. The cheek and/or lip generally presses against the paddle 10 and helps to maintain electrode engagement with the gingiva 12.

Figures 2, 3, 4:
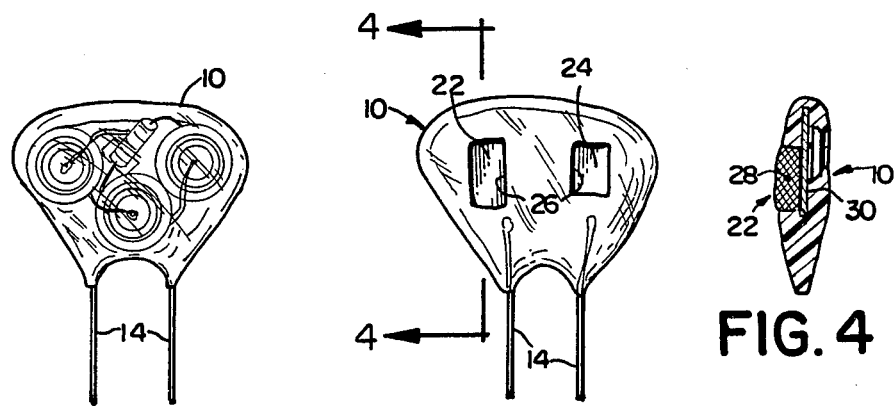
FIG. 2 is an enlarged plan view of one side of an embodiment of the present invention shown in FIG. 1.
FIG. 3 is a plan view of the opposite side of an embodiment shown in FIG. 2.
FIG. 4 is a cross-sectional side view along plane 4—4 of an embodiment shown in FIG. 3 showing portions of an electrode.

FIG. 3 is a plan view showing the opposite side of the paddle 10 shown in FIGS. 1 and 2. FIG. 4 is a cross-sectional side view along plane 4—4 of the paddle 10 shown in FIG. 3. An anode 22 and cathode 24 are shown each in an indentation or well 26 cut or molded into the surface of the paddle 10. Each well 26 is cut or molded into the paddle 10 to dimensions and a depth sufficient to expose the noble metal portion 30 of the anode 22 or cathode 24, and to provide sufficient space for an electrolytic gel 28 to be placed in engagement with the noble metal portion 30 to complete the biocompatible anode 22 or cathode 24, respectively. Generally, each well 26 has a surface area of about 10 mm$^2$, corresponding to the desired size of the electrode.

The anode 22 and cathode 24 are comprised of a noble metal, such as silver and/or palladium. Preferably, the noble metal is an alloy of silver and palladium in a ratio of silver to palladium from about 3:1 to about 8:1. Presently, a ratio of about 6:1 is most preferred. These ratios are believed to exhibit minimal leaching or migration of the silver. It is desirable not to have significant silver migration or leaching from the electrode alloy into the electrolytic gel 28, and through the gel 28 to the gingiva 12. Such migration results in poor biocompatibility and produces undesirable effects, such as lesions, blisters, inflammation and irritation of the gingiva 12. Alloys of silver and palladium demonstrate good aged adhesion and excellent leach resistance. Silver/palladium conductors exhibiting the characteristics described above are commercially available from Cermalloy, Inc. The composition of the noble metal portions 30 of the anode and cathode may be identical.

The gel 28 is preferably comprised of agarose and an electrolyte. Agarose is a purified derivative of agar-agar, which is obtained from certain rhodophytophyta or red algae, commonly called seaweed. Agarose is a natural polysaccharide substantially free of reactive or irritative proteins or other constituents undesirable for biocompatibility. It will be apparent to those skilled in the art that other analogous similarly purified agar derivatives and analogous gel matrices currently available or those being developed may be used for the gel 28.

Agarose is usually available as a dry powder, but may also be available as gel plates or gel beads. Agarose is most commonly used for gel electrophoresis because of its ability to allow rapid diffusion of high molecular weight macromolecules and because of its high gel strength. Agarose is available commercially, for example, from FMC Corp., Marine Colloids Division, Rockland, Ma.

An agarose solution, allowed to gel, may be cut or formed by a mold into pieces suitable for a particular application. In the present invention, it is desirable to cut or form the gelled agarose solution into strips with dimensions that correspond to the metal portion 30 of the anode 22 or cathode 24 exposed by the well 26 cut or molded into the paddle 10.

The electrolytic gel 28 is preferably prepared by dissolving powdered agarose in distilled water in a concentration of about 0.5 mg/100 ml to about 2 mg/100 ml agarose. Below 0.5 mg/100 ml, the gel loses its structural integrity; above about 2 mg/100 ml, the gel is less effective as a medium allowing easy diffusion of electrons. In the present embodiment, an agarose concentration of about 1 mg/100 ml is particularly preferable.

An electrolyte is added to the agarose solution. In the present embodiment, the electrolyte is preferably KCl. KCl is particularly preferable because, in its disassociated ion phase, the mobility of the cation, potassium, and the anion, chlorine, are approximately of the same value. It will be apparent to those skilled in the art, however, that other electrolytes, such as sodium chloride and calcium chloride, may also be used, with strong mono/mono valent electrolytes being preferred.

The concentration of KCl in the preferred embodiment differs between the gel 28 used in the anode 22 and the gel 28 used in the cathode 24. Generally, biocompatibility is better as the concentration of KCl is lowered. However, the efficacy of KCl as an electrolyte in solution decreases as the concentration of KCl approaches zero. It is believed that concentrations as low as about 0.000154 mols in the anode and 0.00154 mols in the cathode are sufficient to provide electrolytic activity preferable for this invention. In addition, it is believed that KCl concentrations as high as 0.005 mols in the anode and 0.05 mols in the cathode will allow ion exchange to occur without undesirable side effects, such as ulceration and laceration of the gingiva. In the preferred embodiment, the concentration of KCl is about 0.00154 mols in the anode and about 0.0154 mols in the cathode.

Experimental observations have shown that gingival environments at the area of the cathode 24 with a pH over about 7.4 pH yielded undesirable effects, such as laceration, irritation, swelling and ulceration of the gingiva 12. It was discovered that gel 28 in the cathode 24 with a pH of about 6.5 pH to about 7.4 pH yielded desirable biocompatible results. In the preferred embodiment, the pH in the gel 28 at the cathode 24 is about 7.2 pH.

To reduce the pH of the agarose/$H_2O$/KCl solution, typically a basic solution, a weak, biocompatible acid, such as citric acid, is added drop-wise until the solution reaches a pH in the range specified above. It will be apparent to one skilled in the art that other weak acids, particularly fruity acids, may be used in conjunction with or as a substitute for citric acid.

In the present embodiment, it is desirable to create and pass a direct current across the cathode 24 and anode 22 with a density of about 0.5 $uA/mm^2$ to about 6 $uA/mm^2$ to stimulate osteoblasty and osteoclasty. The gingiva 12, with which the gel 28 of the anode 22 and cathode 24 are engaged, completes the circuit, allowing such direct current to flow. It is believed, however, that alternating current may also be employed to stimulate osteoblasty and osteoclasty. It will be apparent to those skilled in the art that, if alternating current is applied, both electrodes preferably would be comprised of elements allowing biocompatibility as an anode and a cathode. It is believed that an electrode with a gel portion 28 comprising an agarose aqueous solution of an about 1 mg/100 ml concentration having a pH of about 7.2 pH and about 0.00154 mols of KCl would be preferable in an alternating current embodiment.

It is presently intended, although not critical to the present invention, that a Wilson Mirror circuit be employed to create and apply such current across the cathode 24 and anode 22. The Wilson Mirror is known in the art and used where Field Effect Transistor or FET systems are desirable. The Wilson Mirror is produced by Texas Instruments for constant current applications, for example. It will be apparent to those skilled in the art that analogous FET systems or analogous transistor circuits may be used for the current source.

Current is generated by a cell source, which is connected to the circuit by wires or analogous conductive materials known in the art. Watch batteries are known in the art as one such cell source where small size is desirable. In the preferred embodiment, Varta V317 1.55 V silver watch batteries or their equivalent are used. Such batteries are widely available commercially. It will be appreciated by those skilled in the art that analogous cell sources may be used. Cell size and quantity is dependent uon cell output, the size of the patient's mouth and concerns for the patient's comfort.

A current density less than 0.5 $uA/mm^2$ is not desirable for stimulating the osteoblastic and osteoclastic activities desired for tooth movement. Current densities above 6 $uA/mm^2$ are believed to produce non-biocompatible effects, such as ulceration, laceration, irritation and swelling. A current density of about 2 $uA/mm^2$ is most preferable. However, as will be appreciated by those skilled in the art, the direct current density may be greater or less than 2 $uA/mm^2$, depending upon the number of teeth to be repositioned, the size and relative density of the epithelial gingiva, as well as other factors.

It will be appreciated by those skilled in the art that the present invention may be embodied in other specific forms without departing from the spirit or central attributes thereof and, accordingly, reference should be made to the appended claims, rather than foregoing specification, as indicating the scope of the invention.

We claim:

1. In a method of orthodontic electroosteogenesis, whereby at least one tooth is repositioned in vivo, comprising placing an anode in engagement with epithelial gingiva at a position adjacent to the tooth to be repositioned, placing a cathode in engagement with ephithelial gingiva at a position adjacent to the tooth to be repositioned, and applying electric current between the cathode and anode, wherein the improvement comprises: providing a biocompatible anode having a noble metal portion in engagement with an electrolytic gel portion comprising agarose and an electrolyte, the gel portion being in engagement with the gingiva at an area of osteoclastic or osteoblastic activity; and providing a biocompatible cathode having a noble metal portion in engagement with an electrolytic gel portion comprising agarose, an electrolyte and a weak, biocompatible acid, the gel portion being in engagement with the gingiva at an area of osteoblastic or osteoclastic activity.

2. The method according to claim 1, wherein the gel portion of the anode is in engagement with the gingiva at an area of osteoclastic activity and the gel portion of the cathode is in engagement with the gingiva at an area of osteoblastic activity.

3. The method according to claim 1, wherein the noble metal comprises a silver/palladium alloy.

4. The method according to claim 3, wherein the ratio of silver to palladium is about 3:1 to about 8:1.

5. The method according to claim 3, wherein the ratio of silver to palladium is about 6:1.

6. The method according to claim 1, wherein electric current is applied across the cathode and anode to stimulate osteoclastic and osteoblastic activities.

7. The method according to claim 6, wherein the electric current is direct current.

8. The method according to claim 7, wherein the electric current has a density of about 0.5 uA/mm$^2$ to about 4 uA/mm$^2$.

9. The method according to claim 7, wherein the electric current density is about 2 uA/mm$^2$.

10. The method according to claim 1, wherein the electrolyte is KCl.

11. The method according to claim 10, wherein the concentration of KCl in the cathode gel is about 0.00154 M to about 0.05 M.

12. The method according to claim 10, wherein the concentration of KCl in the cathode gel is about 0.0154 M.

13. The method according to claim 10, wherein the concentration of KCl in the anode gel is about 0.000154 M to about 0.005 M.

14. The method according to claim 10, wherein the concentration of KCl in the anode gel is about 0.00154 M.

15. The method according to claim 1, wherein the acid is citric acid.

16. The method according to claim 15, wherein the citric acid is present in an amount sufficient to lower the pH of the agarose to a pH of about 6.5 to 7.4.

17. The method according to claim 15, wherein the citric acid is present in an amount sufficient to lower the pH of the agarose to a pH of about 7.2.

18. The method according to claim 1, wherein the agarose is in an aqueous solution having an agarose concentration of about 1 mg/100 ml.

19. The method according to claim 1, wherein the noble metal portions of the anode and cathode comprise a 6:1 ratio of silver:palladium alloy, the gel portion of the anode comprises an approximately 1 mg/100 ml aqueous agarose solution containing about 0.00154 M KCl, the gel portion of the cathode comprises an approximately 1 mg/100 ml aqueous agarose solution containing about 0.0154 M KCl and citric acid in an amount sufficient to yield a pH of about 7.2, and the direct electric current density across the cathode and anode is about 2 uA/mm$^2$.

20. The method according to claim 1, further comprising applying force to the tooth in a direction towards which the tooth is to be repositioned simultaneouly with applying the electric current.

21. A biocompatible electrode for electric stimulation, which comprises a noble metal portion in engagement with an electrolytic gel portion, the gel comprising agarose, an electrolyte and a weak, biocompatible acid.

22. The biocompatible electrode according to claim 21, wherein the noble metal comprises a silver/palladium alloy.

23. The biocompatible electrode according to claim 22, wherein the ratio of silver to palladium is about 6:1.

24. The biocompatible electrode according to claim 21, wherein the electrolyte is KCl.

25. The biocompatible electrode according to claim 21, wherein the agarose is an aqueous solution having an agarose concentration of about 1 mg/100 ml.

26. The biocompatible electrode according to claim 21, wherein said acid is citric acid present in an amount sufficient to lower the pH of the agarose to about 6.5 to 7.4.

27. A biocompatible electrode for electric stimulation, which comprised a noble metal portion in engagement with an electrolytic gel portion, the gel comprising agarose and an electrolyte.

28. The biocompatible electrode according to claim 27, wherein the noble metal comprises a silver/palladium alloy.

29. The biocompatible electrode according to claim 28, wherein the ratio of silver to palladium is about 6:1.

30. The biocompatible electrode according to claim 27, wherein the electrolyte is KCl.

31. The biocompatible electrode according to claim 27, wherein the agarose is an aqueous agarose solution having an agarose concentration of about 1 mg/100 ml.

32. Apparatus for electrically stimulating orthodontic osteogenesis comprising at least two electrodes according to claim 27, a current source, circuit means electrically connecting said electrodes to said current source, and support means for holding said electrodes, current source and circuit means in position against the gingiva of a patient undergoing orthodontic treatment.

33. Apparatus according to claim 32, wherein said support means comprises body means for encasing said electrodes, current source and circuit means, and attachment means for non-electrically connecting said body means to a tooth.

34. Apparatus according to claim 33, wherein said body means is shaped to conform to the area of gingiva against which the apparatus is positioned.

35. Apparatus according to claim 33, wherein said body means includes recess means for exposing the noble metal portions of said electrodes and for holding said gel in electrical contact between said noble metal portions and the gingiva.

36. Apparatus according to claim 33, wherein said attachment means comprises at least one prong extending from said body means, said prong being adapted for connection to an ortho bracket on a tooth.

* * * * *